United States Patent [19]

Nealis

[11] Patent Number: 5,445,650
[45] Date of Patent: Aug. 29, 1995

[54] TEMPOROMANDIBULAR JOINT PROSTHESIS

[76] Inventor: Michael F. Nealis, 2829 Babcock Rd., Suite 607, San Antonio, Tex. 78229

[21] Appl. No.: 863,570

[22] Filed: May 20, 1993

Related U.S. Application Data

[63] Continuation-in-part of Ser. No. 673,971, Mar. 21, 1991, abandoned.

[51] Int. Cl.6 .............................................. A61F 2/30
[52] U.S. Cl. ....................................................... 623/18
[58] Field of Search ........................ 623/16, 18, 11, 12; 606/72, 69, 70, 71; 433/172, 173

[56] References Cited

U.S. PATENT DOCUMENTS

| | | |
|---|---|---|
| 3,178,728 | 4/1965 | Christensen ............................ 623/16 |
| 3,579,643 | 5/1971 | Morgan ................................... 623/16 |
| 4,502,161 | 3/1985 | Wall ........................................ 623/16 |
| 4,693,722 | 9/1987 | Wall ........................................ 623/16 |
| 4,778,472 | 10/1988 | Homsy .................................... 623/16 |
| 4,917,701 | 4/1990 | Morgan ................................... 623/16 |

Primary Examiner—David Isabella
Attorney, Agent, or Firm—Glenna Hendricks

[57] ABSTRACT

A total temporomandibular joint prosthesis for the replacement of the mandibular condyle. The prosthesis including an elongated plate having openings for attachments to the mandible. The plate having a shape such that the lateral and inferior edges of the plate are aligned substantially parallel to the lateral and inferior aspects of the mandible and the openings interface only with the lateral surface of the mandible. The prosthesis includes an artificial condyle that is attached to an elongated neck portion extending from the upper end of the plate.

8 Claims, 5 Drawing Sheets

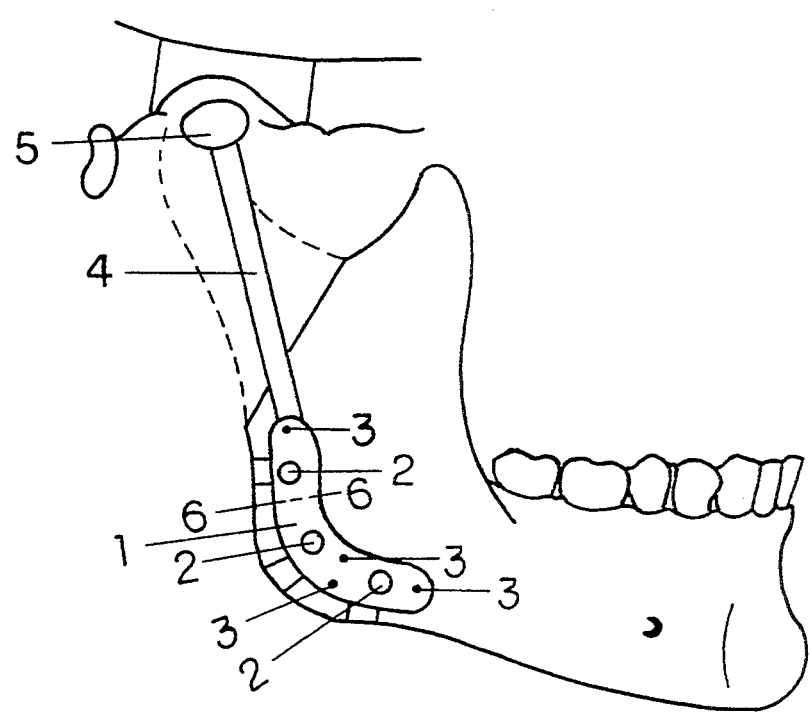
FIG. 5(a)
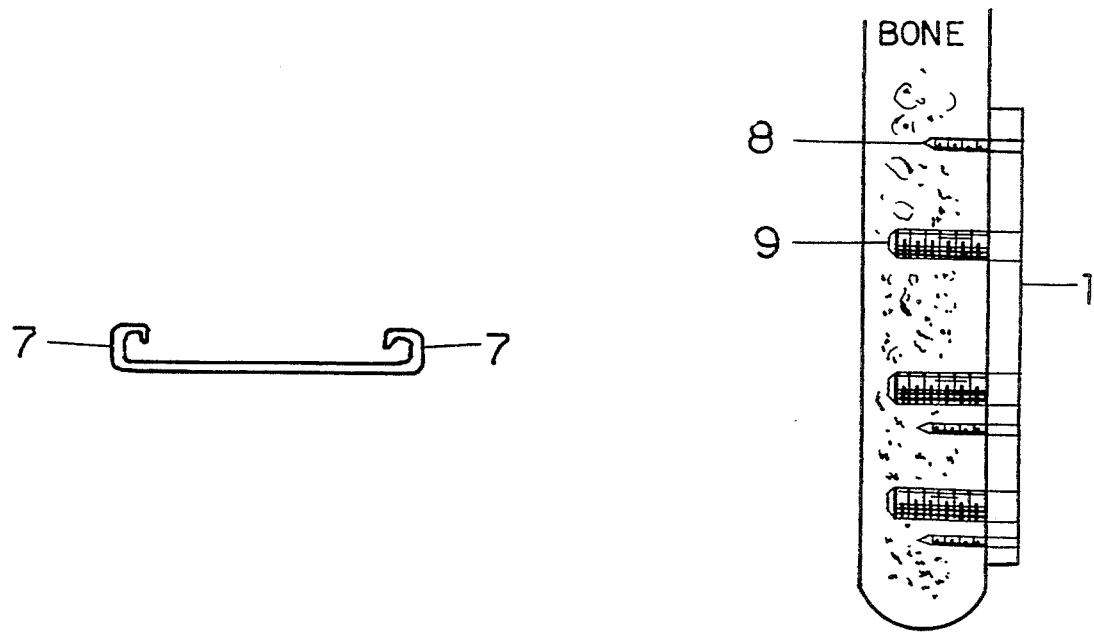
FIG. 5(b)
FIG. 5(c)

TEMPOROMANDIBULAR JOINT PROSTHESIS

This application is a continuation-in-part of U.S. patent application Ser. No. 07/673,971 filed Mar. 21, 1991, now abandoned, and PCT Application PCT/US92/02080 filed Mar. 20, 1992.

FIELD OF THE INVENTION

This invention relates to devices and methods for replacement of temporomandibular joints. Other aspects of the invention include fasteners and methods of implanting a temporomandibular joint replacement device. The new method avoids complications previously common in TMJ replacement procedures by minimizing the surgical manipulation in areas containing major nerves and arteries.

BACKGROUND OF THE INVENTION

The temporomandibular joint consists of the glenoid fossa, the condyle of the mandible, the disc between the fossa and condyle, and the musculoskeletal attachments of these structures. The mandibular fossa does not normally act as a part of a functional joint, but acts as a seat in which the condyle head moves or rests when the mouth is opened and shut. Injury or disease may affect the joint resulting in disfunction and severe pain. While many patients can be treated by nonsurgical methods, individuals who do not respond to such methods must be treated by surgical means. Surgical treatment using various implants has been the preferred method of treatment for those who do not respond favorably to more conservative treatment. Several of these implants have been described in the patent literature.

U.S. Pat. No. 3,178,728 to Christensen describes an implant of a metal fossa that was commonly used for treatment of ankylosis. The prosthesis was contoured to fit within the glenoid fossa and was shaped to overlay the articular eminence. The prosthesis was used extensively for treating cases of joint arthrosis or fibrous ankylosis.

U.S. Pat. No. 3,579,643 to Morgan discloses a device in the form of a sheet-like element contoured to overlay the articular eminence of the glenoid fossa.

U.S. Pat. Nos. 4,502,161 and 4,693,722 to Wall describe a prosthetic substitute for the condyle of the mandible which is used in conjunction with a prosthetic meniscus. The condyle is first removed surgically. The prosthetic condyle component comprises two plates between which is sandwiched the ramus of the mandible below the condylectomy site. One of the plates extends upward to form the prosthetic condyle having a convex surface. The method of surgical treatment taught therein requires extensive surgical intervention in an area containing the internal maxillary and masseteric arteries, the mandibular nerve and the branches of the facial nerve. The prosthetic meniscus used with the prosthetic condyle comprises a resilient insert shaped to be received in the glenoid fossa.

U.S. Pat. No. 4,917,701 to Morgan describes and claims a temporal implant component which is a thin, rigid plate contoured to generally conform to and overlay at least part of the articular eminence and mandibular fossa of the glenoid fossa. The component does not overlay the petro-tympanic fissure. A resilient, biologically inert material is securely attached to the superior surface of the rigid plate so that the resilient material is disposed to reside between the rigid plate and the floor of the mandibular fossa. The condyle prosthetic component disclosed therein comprises a thin, generally upright channel having a condyle molded of plastic material attached to the channel. The channel is shaped to slip over and wrap around the posterior border of the ramus from which the natural condyle has been removed. The area subjected to manipulation during the surgical procedure is the same as that of U.S. Pat. No. 4,693,722 of Wall. Hence, the problems related to site of surgical intervention discussed above are not avoided by the methods of Morgan.

U.S. Pat. No. 4,778,472 to Homsy, et al. describes and claims a temporomandibular prosthesis wherein the prosthetic condyle articular face with a heel extending backwardly from the face and a toe extending forwardly from the face. The condyle is shown as a part of a component having a plate which is attached in the region of the ramus. There is no disclosure of how the plate is to be attached to the mandible. In fact, there is no disclosure of the surgical procedure required to implant the device. Moreover, several complications have arisen as a result of using the device of Holmsy, et al., including, but not limited to, the disintegration of the PROPLAST with resulting injurious tissue response.

U.S. Pat. No. 4,936,852 to Kent, et al. discloses a minicondyle that covers a natural condyle wherein the diseased portion has been excised. It is asserted in that disclosure that the use of the mini prosthesis of the invention optimized the TMJ function through improved adaptability during surgery. However, the area in which the surgical activity is performed is in the region of the internal maxillary artery and a branch of the facial nerve.

European patent publication 290-138-A of Pollock describes a set of fasteners for holding bone together. There is no teaching therein that the fasteners decribed therein would be appropriate for use to support an artificial condyle or any other prosthetic device.

SUMMARY OF THE INVENTION

The instant invention provides a means of replacing the condyle of the temporomandibular joint with minimal surgery in areas adjacent to major nerves and arteries. Because the insertion of the attachment to the bone of the mandible is a plate that is parallel to the angle of the mandible in an area with minimal supply of major arteries and nerves, it is possible to perform surgery with less risk to the patient. In the preferred embodiment, the plate is affixed to the mandible with two sets of fastener means. The first set is a temporary means for holding the plate in place for the first few weeks and months while the second provides a fastener that has a bioactive coating which serves as a starter layer for osteogenesis.

The condyle portion of the prosthetic device may be made to form one piece with the plate or may be provided as a separate unit adapted for attachment to the plate during surgery. In the latter case, when neck of the condyle portion may be adapted for attachment to the plate portion during surgery, it is possible to position the plate, then choose the condyle portion that is the best size and shape for the patient during surgery. In another embodiment the neck portion of the condyle may be made as one unit with the plate and the condyle may be chosen during surgery and attached to the neck at time of placement of the plate.

The invention also encompasses a novel fossal prosthesis that can be trimmed to fit in the patient during surgery. However, the condyle prosthetic component and the fossal component can be used separately with other components known in the art.

BRIEF DESCRIPTION OF THE DRAWINGS

FIG. 5(a) is a view of the mandible with the implanted replacement of the invention wherein the area bounded by—indicates the outline of the condyle and condyle neck which have been excised. FIG. 5(b) is a sectional view of the plate along the line 6—6. FIG. 5(c) is a posterior view of the mandible with screws in place wherein (1) identifies the plate, (8) indicates the immediate stabilization fasteners and (9) indicates the osseointegrated fasteners.

DETAILED DESCRIPTION OF THE INVENTION

Figure 1:
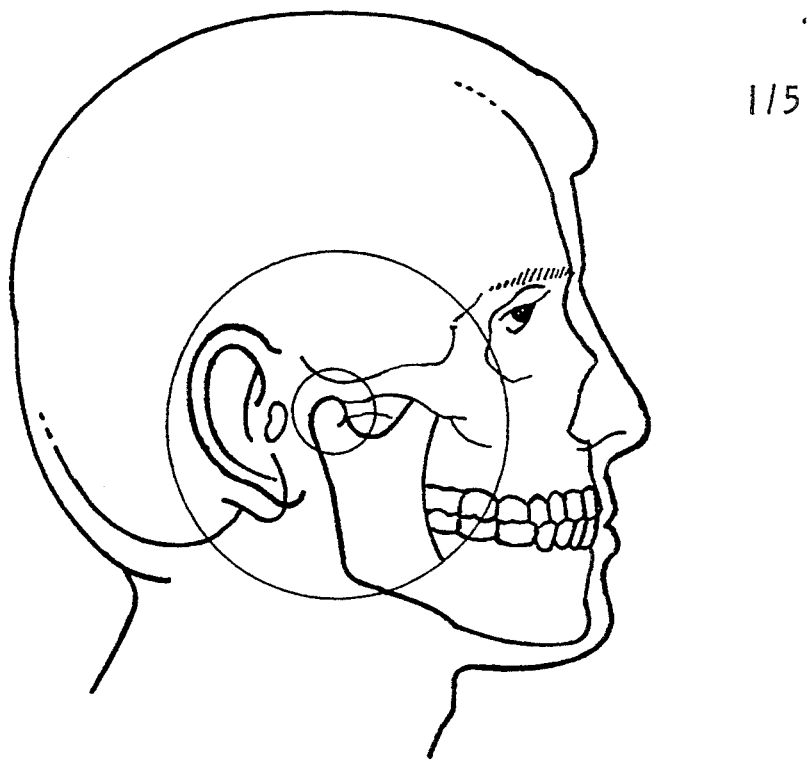
FIG. 1 is a view of the anatomical structure of the operative region.
Figure 2:
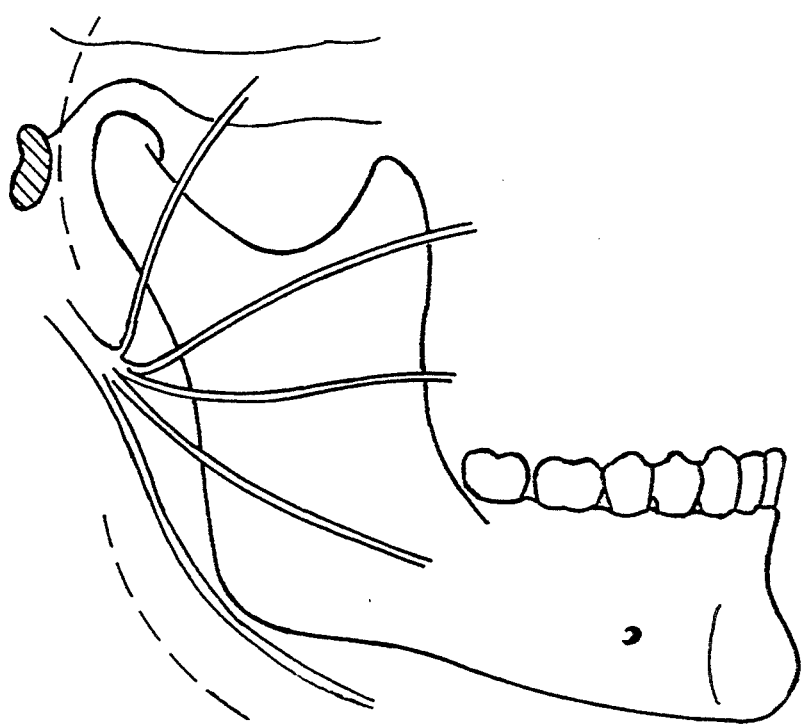
FIG. 2 is a view of the of the mandible showing the location of the facial nerve.
Figure 3:
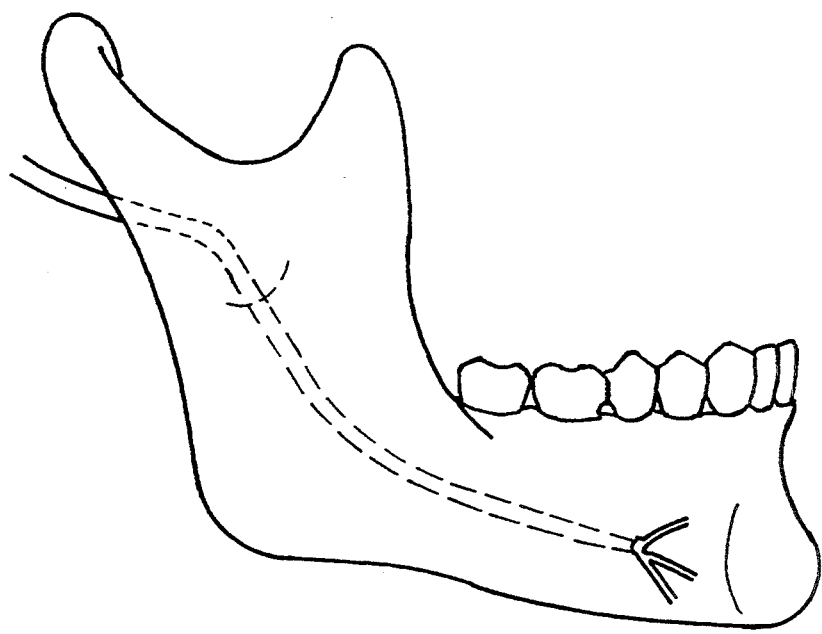
FIG. 3 is a view of the mandible showing the location of the mandibular nerve.
Figure 4:
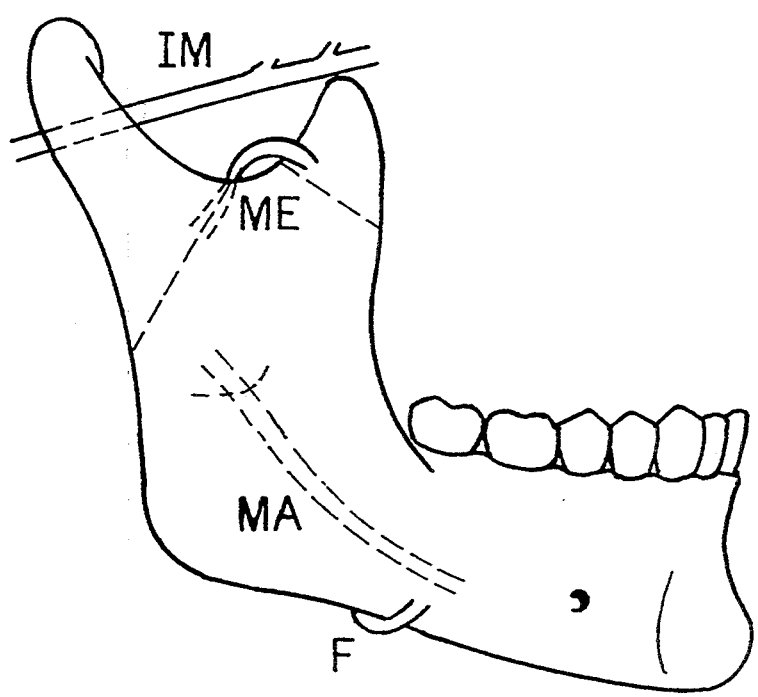
FIG. 4 is a view of the mandible showing the major arteries. IM indicates the internal maxillary artery, ME indicates the masseteric artery, MA designates the mandibular artery, and F designates the facial artery.
Figure 6A:
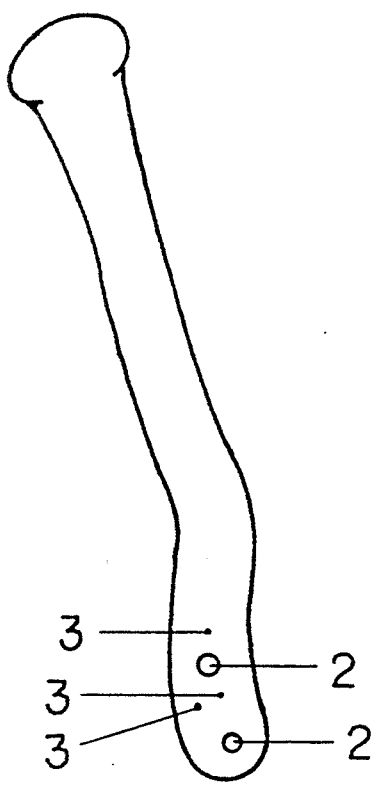
FIG. 6 (a) is a view of the condyle portion with the extension of the neck to fit into the channel of the plate portion. Numbers 2 and 3 represent fastener openings as indicated in FIG. 5.
FIG. 6(b) is a view of the one piece condyle replacement unit.
Figure 6B:
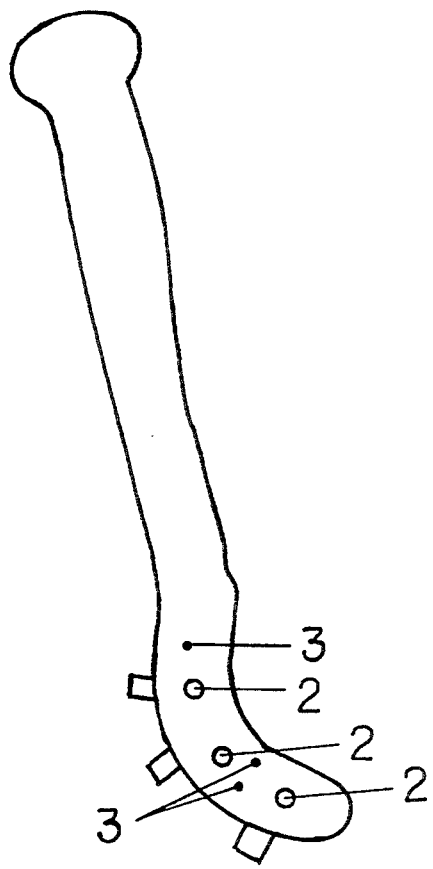

The invention provides the means of implanting a prosthetic condyle component wherein the danger of damage to major nerves and blood vessels in the region is minimized though use of a plate implanted in an area of the mandible. The surgery in accord with the use of the implant requires first that a condylectomy be performed with the excision occurring in the region of the neck of the condyle. Referring to the figures, FIG. (a) is a view of the mandible with the implanted replacement of the invention wherein the area bounded by—indicates the outline of the condyle and condyle neck which have been excised. The drawings have been numbered so that a given number, whether in FIGS. 5, 6, or 7, always refers to the same structure. In FIG. 5, 1 always refers to the plate attached to the lower mandible, 2 refers to implant fastener openings, 3 identifies smaller immediate fastener openings, 4 identifies the nec of the condyle, 5 indicates the head of the condyle, 6—6 is a line identifying a particular cross-section. FIG. 5 (b) is a sectional view of the plate along the line 6—6 showing the channel having ridges (7) for acceptance of the extension from the neck of the condyle. FIG. 5 (c) is a posterior view of the mandible with screws in place wherein 1 identifies the plate, 8 indicates the immediate stabilization fasteners and 9 indicates the osseointegrated fasteners. An outline of the region that might be excised is circumscribed by the line designated—in FIG. 5(a). The exact site at which the amputation of the condyle occurs will vary as required by the patient's disease condition.

The plate having fastener openings for attachment to the mandible is shaped so that it extends upward parallel with the posterior boarder of the mandible and then extends forward at an angle so that the edge of the plate is about parallel with the inferior boarder of the mandible. Hence, the lateral/inferior edge of the plate is parallel with the lateral/inferior aspects (otherwise defined as the posterior and inferior boarders) of the mandible. (See FIG. 5 (a)) The forward edge of the plate lies lateral and posterior to the midline of the mandible which separates the left and right sides of the mandible. In the preferred embodiment, the plate lies on the lateral aspect of the mandible and does not extend beyond the area which overlays the facial artery.

The condyle portion with the neck and artificial condyle with the plate may be made as one implantable unit. In another embodiment of the invention, the condyle portion may be made as a unit separate from the plate, said condyle portion being adapted for attachment to the plate during surgery. When the condyle prosthetic device is composed of two components it is possible to position the plate and fix it in position on the mandible with the immediate fastening means. The surgeon would then choose from among a collection of condyle components the best size component for attachment to the fixed plate.

The separate condyle portion may be attached to the plate through screws into the plate and/or other coupling means known in the art. The extension for fastening to the plate may have fastener openings for implant fasteners to permit placement of the implant fasteners though both the plate and the extended neck portion using implants that extend through the plate and extended neck portion into the mandible. Placement and attachment are facilitated when the plate is equipped with a means of positioning or fastening the neck to the plate itself. One such means is illustrated in FIG. 5 (b) as a channel for acceptance of the extension from the artificial condyle neck. The neck could have fastener openings that would, upon placement in the channel, align with the comparable fastener openings in the plate.

In another embodiment of the invention, the condyle neck portion extends as one piece from the plate and has, at its superior terminus, an orifice for acceptance of a protrusion from a separate component which comprises the condyle head having a protrusion and fastening means for attachment to the terminus from the neck portion. The fastening means may be a threaded, freely rotating rim portion surrounding the protrusion for attachment over the threaded terminus of the neck extending from the plate attached to the mandible.

The use of the plate as the site of attachment of the prosthetic component allows the surgeon to avoid damage to the facial nerve. Access to the bone is accomplished by tunnelling under the soft tissue to avoid damage to the facial nerve above. The end of the anterior arm of the plate falls posterior to the facial artery and the attachment of the plate is inferior to the mandibular artery.

The plate (1) in FIG. 5 containing small and large fastener openings is positioned and attached during surgery with small metal fasteners in the body of the plate and the stabilization tabs provide stability during the remainder of surgery. Larger implant fasteners (2) treated with bioactive materials such as hydroxyl apatite are placed in the larger fastener openings to provide long term osseointegrated fixation of the plate. These fasteners will become secured through osteogenesis at the bioactive layer. However, the small fasteners will hold the plate in place until the osteogenesis has occurred at the implant sites. The fasteners are about 6 to 10 millimeters long, depending on the thickness of the plate. The implants are about the same length as the immediate fasteners. Both the immediate fasteners and the implants are made of a rigid metal. A preferred metal is titanium such as T160. The implant fasteners are coated with plasma or hydroxyl apatite. (See examples 1 and 2 for a procedure for a preferred embodiment.) The implants may be threaded throughout the entire length of the shank.

The plate may be made of any suitable biocompatible material of suitable strength and weight. Vitallium, titanium of sufficient strength, cobalt-chromium-molybdenum alloys, and stainless steel are appropriate materials for making the plate and the condyle. The neck and head of the condyle portion can be made of materials other than those used for the plate. Examples of such materials are hard, smooth, biocompatible plastic materials such as high molecular weight polyethylene (HMWPE) or acrylic.

The face of the plate can be rendered bioactive in the same manner as the implants and the mandibular plate through application of a plasma spray or application of hydroxyl apatite or both as taught in U.S. Pat. No. 4,702,930, which is incorporated herein by reference in its entirety.

While various shapes for articulating surfaces of the condyles have been disclosed in the literature, the preferred shapes for use in accord with the teachings of the invention are either rounded or elongated, tapered heads. A head having symmetrical curvature is easier to position and can be more widely used, since the condyle and fossa are more readily interchanged. The use of material such as polymers that can be sculped for the surface of the superior fossa which interfaces with the bone of the fossal cavity makes it possible to adapt the prosthesis to the patient during surgery. Furthermore, when materials such as bone cement are used to secure the fossal implant the adhesive adapts to and fills any spaces between the bone and the prosthesis to provide secure fit.

While it is not essential to the practice of the invention to use the dual fixation system described herein, the use of the dual fixation means presents several advantages. The small screws provide immediate fixation. After the plate is placed in position, the surgeon can evaluate the fit of the entire prosthesis before drilling the holes for the long term implant screws occurs. If the larger holes are improperly placed, it is difficult to effect a change in position after further evaluation of the alignment of the prosthesis. However, the smaller screws can be removed and the plate realigned during surgery. The smaller screws also provide support during the time oseointegration of the implants is in progress.

EXAMPLE 1

To provide the plate with a bioactive surface, a plate of titanium in accord with the configuration depicted in FIG. 5 is etched on the posterior face. A layer of hydroxyl apatite is then applied onto the etched metallic surface. The surface is then subjected to compacting by hot isostatic pressing, with the pressure of more then 1 kbar and at a temperature of 400° C. The surface of the plate is then cleaned and dehydrated by intensive ion bombardment down to a depth of about 0.2 um.

EXAMPLE 2

Threaded implants for placement in the large fastener openings are treated in the matter described in example 1.

Figure 7A:
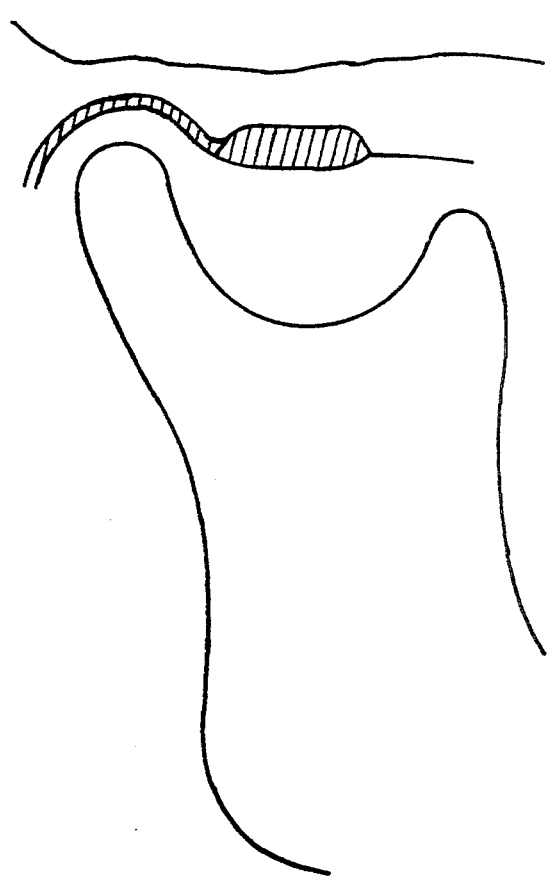
FIG. 7(a) is a view of a fossal prosthesis in place.
Figure 7B:
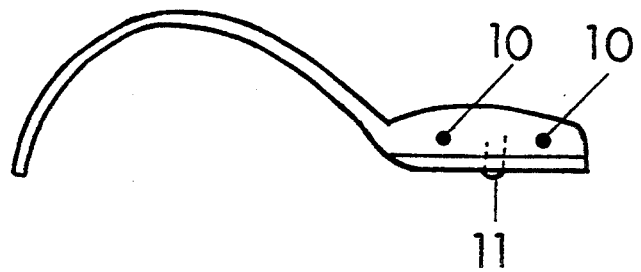
FIG. 7(b) is an enlargement of the fossal prosthesis showing the screws into the lateral aspect of the zygoma (10) and into the inferior aspect of the zygomatic arch (11).

A preferred embodiment of the invention utilizes a novel fossal prosthesis having a weight-bearing surface formed of a thin, rigid plate contoured of rigid biologically inert material such as cobalt-chromium alloys, titanium, high molecular weight polyethylene (HMWPE), or stainless steel (FIG. 7 (a) and (b)). The HMWPE is a particularly useful material for this purpose, since it can be trimmed to fit the particular patient's fossa during the surgical procedure. In another preferred embodiment, the plate is composed of sandwiched materials wherein the plate is overlaid on its superior surface (the surface that interfaces with the patient's natural fossa) with a less rigid material than the material at the weight-bearing surface. For example, the superior surface disposed to ride between the more rigid surface and the floor of the natural fossa may be made from high molecular weight polyethylene while the surface exposed to the condyle could be made from titanium.

In another preferred embodiment, the artificial fossa is of a sandwiched construction wherein the superior surface is a metal such as titanium and the inferior surface that interfaces with the condyle is a hard, non-metallic material such as high density polymer. High molecular weight polyethylene (HMWPE) is a preferred material. The superior surface of the metal that interfaces with the bone can be treated to provide oseointegration of the fossal prosthesis with the bone. (See method of example 1.)

The plate of the artificial fossa has a lateral flange that extends to conform to the lateral zygoma and underlays the zygomatic arch. The flange contains fastener openings. In a preferred arrangement the flange contains fastener openings on the face conforming to the lateral aspect of the zygoma and at least one fastener opening on the aspect of the flange underlying the zygomatic arch. The openings may be of differing sizes to accept small fasteners to provide immediate stability and to accept larger implant fasteners treated with such bioactive materials as hydroxyl apatite or plasma spray. A preferred material for the fasteners is a rigid titanium such as T160. Screws are approximately 6 to 10 millimeters in length and 2 millimeters in diameter.

When both artificial condyle and fossa are implanted, it is desireable that polymeric and metallic surfaces be in contact at the fossal/condyle interface. Hence, if the fossal surface at this interface is HMWPE, the condyle head would be of metal.

Before placement of the fossal prosthesis, both the bone and the prosthesis may be sculpted to provide proper fit of the prosthetic device.

The surface area of the superior surface of the plate may be enlarged by known means such as dimpling to facilitate adhesion of the plate to the glenoid fossa. Adhesives commonly used in orthopedic and dental surgery such as bone cement can be applied to the superior surface of the artificial fossa and/or to the surface of the natural fossa to secure the artificial fossa in place.

The condylar component of the invention can, however, be used with any appropriate temporal component. One suitable component is the temporal component disclosed by Morgan in U.S. Pat. No. 4,917,701. The temporal component of that patent comprises a thin, rigid plate of biologically inert material contoured to generally conform to and overlay at least a part of the mandibular fossa portion of the glenoid fossa. A layer of resilient, biologically inert material is securely attached to the superior surface of the plate and is disposed to reside between the plate and the floor of the mandibular fossa.

The art also teaches several glenoid fossa implants of more flexible and resilient materials. (See U.S. Pat. No. 4,693,722 to Wall, which is incorporated herein by reference.) However, the more preferred glenoid fossa implants have a smooth metallic surface that interfaces with the condyle portion of the prosthesis. The use of very strong material for the fossa is imperative in order to prevent damage to the fossa and the underlying soft tissue.

In order to standardize the components of the artificial TMJ disclosed herein, the rounded shape is preferred both for the fossal weight-bearing surface and for the head of the artificial condyle.

The components of the invention, including the fastening means, may be provided in kit form. Separate kits would be available for the left and right prosthetic replacement and would contain the plate and condyle section either as one piece or as separate parts. If the condyle and neck portion is separate from the plate, coupling devices might be included. The fossa prosthesis may be packaged with the condyle prosthesis or provided as a separate kit with necessary fastener means.

I claim:

1. A temporomandibular prosthesis for replacement of the mandibular condyle of the temporomandibular joint having lateral and inferior aspects comprising:
    an elongated plate configured and having openings therein for attachment to the mandible, said plate being shaped in such a manner that the lateral and inferior edges of said plate, when attached to the mandible, are aligned substantially parallel to the lateral and inferior aspects of the mandible, and wherein the openings interface only with the lateral surface of the mandible; and
    an artificial condyle attached to an elongated neck portion, said neck portion extending from the upper end of said plate.

2. A prosthetic device of claim 1 wherein the neck and artificial condyle are made of metallic material.

3. A prosthetic device of claim 1 wherein the neck portion has hastener openings.

4. A prosthetic device of claim 1 wherein there are two sizes of fastener openings.

5. A prosthetic device of claim 2 wherein the plate is made from titanium 160.

6. A prosthetic device of claim 4 having fastener openings on the neck portion adapted for acceptance of implant fasteners.

7. A prosthetic device of claim 4 wherein the openings of smaller size are adapted for accepting fasteners for immediate fixation.

8. A prosthetic device of claim 4 wherein the opening of larger size are adapted for accepting implant fasteners.

* * * * *